(12) United States Patent
Rossi et al.

(10) Patent No.: US 11,739,174 B2
(45) Date of Patent: Aug. 29, 2023

(54) CATIONIC CYCLIC AMINE AND AMPHIPATHIC TRANSFECTION REAGENTS

(71) Applicant: Mirus Bio LLC, Madison, WI (US)

(72) Inventors: Nicholas A. A. Rossi, Madison, WI (US); Anatoly Pinchuk, Fitchburg, WI (US); Karen Neder, Madison, WI (US); James Ludtke, Madison, WI (US); Laura Juckem, Madison, WI (US)

(73) Assignee: Mirus Bio LLC, Madison, WI (US)

( * ) Notice: Subject to any disclaimer, the term of this patent is extended or adjusted under 35 U.S.C. 154(b) by 409 days.

(21) Appl. No.: 16/797,967

(22) Filed: Feb. 21, 2020

(65) Prior Publication Data

US 2021/0269570 A1 Sep. 2, 2021
US 2022/0041778 A9 Feb. 10, 2022

Related U.S. Application Data

(63) Continuation of application No. 14/632,385, filed on Feb. 26, 2015, now Pat. No. 10,619,162.

(51) Int. Cl.
*C08F 226/06* (2006.01)
*C07D 241/04* (2006.01)
*C12N 15/87* (2006.01)

(52) U.S. Cl.
CPC .......... *C08F 226/06* (2013.01); *C07D 241/04* (2013.01); *C12N 15/87* (2013.01)

(58) Field of Classification Search
CPC ...... C08F 226/06; C07D 241/04; C12N 15/87
USPC ........................................................ 435/440
See application file for complete search history.

(56) References Cited

U.S. PATENT DOCUMENTS 5,055,517 A * 10/1991 Shorr ............... G01N 27/44747
524/916
10,619,162 B1 4/2020 Rossi

* cited by examiner

*Primary Examiner* — Ling Siu Choi
*Assistant Examiner* — Ronald Grinsted
(74) *Attorney, Agent, or Firm* — Wilson Sonsini Goodrich & Rosati

(57) ABSTRACT

Cationic cyclic amine containing polymers and copolymers as well as novel lipids have been designed and synthesized for efficient delivery of nucleic acids to cells in biological systems, specifically for in vitro cell transfection research.

20 Claims, 12 Drawing Sheets

General scheme and structures:

where $R_1$, $R_4$ = H, $CH_3$ $R_2$, $R_3$ = $(CH_2)_x$, where x = 1 - 6

X = $NH(CH_2)_x$, $O(CH_2)_x$ where x = 0 - 6

Y = N, CH where $R_1$, $R_4$ = H, $CH_3$ $R_2$, $R_3$ = $(CH_2)_x$, where x = 1 - 6

X = $NH(CH_2)_x$, $O(CH_2)_x$ where x = 0 - 6

Y = N, CH

General scheme and structures:

where $R_1$, $R_4$ = H, $CH_3$ $R_2$, $R_3$ = $(CH_2)_x$, where x = 1 - 6

X = $NH(CH_2)_x$, $O(CH_2)_x$ where x = 0 - 6

Y = N, CH where $R_1$, $R_4$ = H, $CH_3$ $R_2$, $R_3$ = $(CH_2)_x$, where x = 1 - 6

X = $NH(CH_2)_x$, $O(CH_2)_x$ where x = 0 - 6

Y = N, CH where $R_1$, $R_4$, $R_5$ = H, $CH_3$ $R_2$, $R_3$ = $(CH_2)_x$, where x = 1 - 6

$R_6$ = alkyl group containing 1 or more primary, secondary, or tertiary amines

X = $NH(CH_2)_x$, $O(CH_2)_x$ where x = 0 - 6

Y = N, CH

Z = NH, O where R$_1$ = H, CH$_3$

R$_2$, R$_3$ = (CH$_2$)$_x$, where x = 1 - 6

X = NH(CH$_2$)$_x$, O(CH$_2$)$_x$ where x = 0 - 6

Y = N, CH where:
each n is an integer from 0 to 1, and
each m is an integer from 2 to 6 where:
each n is an integer from 0 to 1, and
each m is an integer from 2 to 6

3103

3301

1112

1180

CATIONIC CYCLIC AMINE AND AMPHIPATHIC TRANSFECTION REAGENTS

CROSS REFERENCE TO RELATED APPLICATIONS

This application is a continuation application of U.S. application Ser. No. 14/632,385, filed Feb. 26, 2015, now U.S. Pat. No. 10,619,162, the contents of which are all hereby incorporated by reference.

FIELD OF THE INVENTION

The field of the present invention is compounds comprising cationic cyclic amine containing copolymers, novel lipids and the use of such reagents for delivering nucleic acids to a cell.

BACKGROUND

The present invention relates to cationic polymer and lipid compounds which have use in the delivery of nucleic acid to cells in biological systems, for instance in in vitro cell transfection research. The invention also relates to methods of making such compounds and potentially to gene therapy using such compounds.

The control of living processes is mediated through nucleic acids. Nucleic acids encode proteins which, as enzymes, hormones and other regulatory factors, carry out the processes which enable living organisms to function. Nucleic acids also encode for regulatory sequences which control the expression of proteins.

Because of its central role in living organisms, nucleic acids make an ideal therapeutic target. It is thought that many diseases could be controlled by the manipulation of nucleic acids in living organisms.

The key factor limiting therapies based on nucleic acid manipulation is the ability to deliver nucleic acids to the appropriate compartment of the cells. Nucleic acids are fragile molecules which are highly negatively charged (one negative charge per phosphate group) and which are readily cleaved by nucleases present both in extracellular fluids and intracellular compartments. As a highly charged molecule it will not cross the lipid membranes surrounding the cell, nor can it readily escape from endosomal compartments involved in the uptake of macromolecules into cells. Even RNAi molecules, although smaller in molecular weight, show significant problems of stability and uptake.

The efficient delivery of biologically active compounds to the intracellular space of cells has been accomplished by the use of a wide variety of vesicles. One particular type of vesicle, liposomes, is one of the most developed types of vesicles for drug delivery. Liposomes, which have been under development since the 1970's, are microscopic vesicles that comprise amphipathic molecules which contain both hydrophobic and hydrophilic regions. Liposomes can be formed from one type of amphipathic molecule or several different amphipathic molecules. Several methods have been developed to complex biologically active compounds with liposomes. In particular, polynucleotides complexed with liposomes have been delivered to mammalian cells. After publication of DOTMA (N-[1-(2,3-dioleyloxy)propyl]-N,N,N-trimethylammonium chloride), a number of cationic lipids have been synthesized for this purpose. Essentially all the cationic lipids are amphipathic compounds that contain a hydrophobic domain, a spacer, and positively-charged amine(s). The cationic lipids are sometimes mixed with a fusogenic lipid such as DOPE (dioleoyl phosphatidyl ethanolamine) to form liposomes. The cationic liposomes are then mixed with plasmid DNA and the binary complex of the DNA and liposomes are applied to cells in a tissue culture dish or injected in vivo. The ease of mixing the plasmid DNA with the cationic liposome formulation, the ability of the cationic lipids to complex with DNA and the relative high levels of transfection efficiency has led to increasing use of these formulations. However, these cationic lipid formulations have a common deficiency in that they are typically toxic to the cells in culture and in vivo. More recently lipids have been used in association with other DNA-binding compounds to facilitate cell transfection.

The use of cationic polymers overcomes some, but not all, of the problems associated with cationic lipid formulations. Polycationic polymers are, however, generally cytotoxic although some cationic polymers with lower toxicity have been reported. Cationic polymers are generally cheap to produce, and do not have the shelf life problems associated with cationic lipids.

Cationic polymers are very efficient at condensing nucleic acids into a small volume and at protecting nucleic acids from degradation by serum nucleases. Interaction is through an equilibrium reaction in which adjustment of the environmental conditions, (salt concentration, pH, molecular weight of each of the polymers) will affect the composition and form of the complexes.

In the formation of toroids, the processes of condensation of nucleic acids and aggregation of particles are competing, so that these systems tend to be unstable with time and form larger aggregates. This is influenced by the charge ratio of the complexes, and can be reduced by using an excess of one of the components. Generally such complexes are, therefore, made with an excess of polymer and/or lipid, although similar complexes with an excess of nucleic acids also have some favorable properties.

Cationic polyamines such as polyethylenimine (PEI), poly(L-lysine), polyamidoamines, chitosan, poly(amino ester)s and polyacrylates have been widely investigated as nucleic acid delivery vehicles.

In comparison to cationic polymers containing aliphatic amino moieties, cyclic amine containing polymers has received significantly less or no attention in terms of their development delivery polymers. The cyclic amine moieties exhibit different physical and chemical properties compared to their aliphatic or aromatic counterparts It is an object of the invention to overcome at least some of the above problems.

SUMMARY

Figure 1:
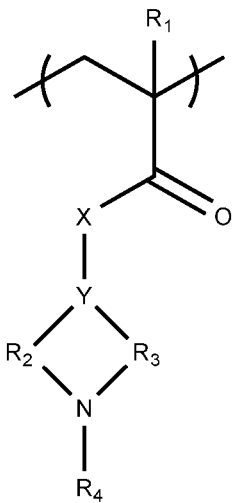
FIG. 1 shows the general structure of cationic cyclic amine containing polymers and copolymers.
Figure 1:
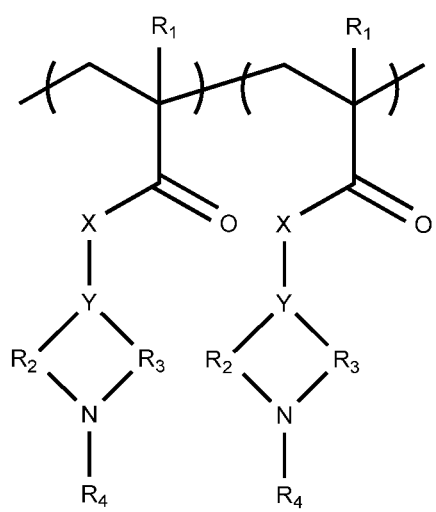

The invention pertains to the use of synthetic cationic cyclic amine containing polymers and copolymers as nucleic acid transfection agents. In some instances, the polycations described are used in conjunction with novel endosomolytic lipids to transfect nucleic acids into cells.

The repeat units of the polycations described here have one or more cyclic amines and can be either secondary or tertiary, or a combination thereof. In one embodiment, the precursor hydroxide or amine unit, and the acrylate or acrylamide monomer containing secondary and/or tertiary cyclic amine side groups are protected with tert-butoxycarbonyl (BOC) protecting moieties. The BOC protected precursors can be used to form homopolymers or various types of copolymers by grafting to a formed macromolecule via the hydroxy or amino functional group. Alternatively, the BOC protected monomers can be used to form homopolymers or various types of copolymers with acrylamide and/or acrylate co-monomers. The BOC groups are subsequently removed under acidic conditions post-modification or post-polymerization to form the required polycations.

The development, synthesis, and characterization of cationic cyclic amine copolymers are described. Various cyclic amine copolymers containing tertiary, secondary, and/or primary amines were synthesized using free radical polymerization. Specifically, reversible-addition fragmentation chain transfer (RAFT) polymerization was used to synthesize polyacrylamides with well-defined structures, compositions, and molecular weights (Mw/Mn<1.5). Architectures include, but are not limited to, random/statistical, gradient, block, linear, branched, cross-linked/network, star, and dendritic structures.

The present invention provides a compound to assist nucleic acid transfer into animal cells via a complex comprising nucleic acid and a cationic cyclic amine containing polymers and copolymers. A novel compound and method of preparation thereof, is described.

In a preferred embodiment, compositions comprising nucleic acids and cationic cyclic amine containing polymers and copolymers and/or lipids, and processes using such compositions to deliver a nucleic acid to an animal cell in vivo or in vitro for the purposes of altering expression of a gene in the cell are described.

In a preferred embodiment, compositions and compounds are described that facilitate delivery of nucleic acid to an animal cell in vitro and in vivo. The nucleic acid comprises a double stranded structure having a nucleotide sequence substantially identical to part of an expressed target nucleic acid within the cell. Further, the use of a cationic cyclic amine containing polymers and copolymers and/or lipids significantly increased nucleic acid transfer efficiency. The nucleic acid then alters expression of a selected endogenous nucleic acid.

In a preferred embodiment, the cationic cyclic amine containing polymers and copolymers and/or lipids is used to assist transfection of DNA, RNA, mRNA or RNAi into a cell. The nucleic acid then alters the cell's natural process.

RNA interference (RNAi) is a phenomenon wherein double-stranded RNA, when present in a cell, inhibits expression of a gene that has an identical or nearly identical sequence. Inhibition is caused by degradation of the messenger RNA (mRNA) transcribed from the target gene. The double-stranded RNA responsible for inducing RNAi is termed interfering RNA. dsRNA introduced into the cytoplasm of a cell is first processed into RNA fragments 21-25 nucleotides long. It has been shown in in vitro studies that these dsRNAs, termed small interfering RNAs (siRNA) are generated at least in part by the RNAse III-like enzyme Dicer. Each siRNA is unwound into two single-stranded (ss) ssRNAs, the passenger strand and the guide strand. The passenger strand is degraded, and the guide strand is incorporated into the RNA-induced silencing complex (RISC). The most studied outcome is post-transcriptional gene silencing, which occurs when the guide strand base pairs with a complementary sequence in a messenger RNA molecule and induces cleavage by Argonaute, the catalytic component of the RISC complex.

RNAi has become a valuable research tool, both in cell culture and in living organisms, because synthetic dsRNA introduced into cells can selectively and robustly induce suppression of specific genes of interest. RNAi may be used for large-scale screens that systematically shut down each gene in the cell, which can help identify the components necessary for a particular cellular process or an event such as cell division. The pathway is also used as a practical tool in biotechnology and medicine. The cationic polyacrylamides described in this specification provide a mechanism to transfect siRNA and other nucleic acids into cells.

The development, synthesis, and characterization of cationic cyclic amine containing polymers and copolymers polymers are described. Various cyclic amine containing polymers and copolymers were synthesized using free radical polymerization. Specifically, reversible-addition fragmentation chain transfer (RAFT) polymerization was used to synthesize polyacrylamides with well-defined structures, compositions, and molecular weights (Mw/Mn<1.5). Architectures include, but are not limited to, random/statistical, gradient, block, linear, branched, cross-linked/network, star, and dendritic structures. RAFT has rivaled other controlled free radical polymerization techniques such as atom transfer radical polymerization (ATRP) as one of the most effective ways to synthesize well-defined and novel polymers. The controlled synthesis of RAFT polymers is achieved using conventional radical initiators such as azobisisobutyronitrile (AIBN), and the reversible chain transfer of dithiocarbonyl compounds.

Polymers: A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft. The main chain of a polymer is composed of the atoms whose bonds are required for propagation of polymer length. The side chain of a polymer is composed of the atoms whose bonds are not required for propagation of polymer length. To those skilled in the art of polymerization, there are several categories of polymerization processes that can be utilized in the described process.

Steric Stabilizer: A steric stabilizer is a long chain hydrophilic group that prevents aggregation of final polymer by sterically hindering particle to particle electrostatic interactions. Examples include: alkyl groups, PEG chains, polysaccharides, alkyl amines. Electrostatic interactions are the non-covalent association of two or more substances due to attractive forces between positive and negative charges.

Buffers: Buffers are made from a weak acid or weak base and their salts. Buffer solutions resist changes in pH when additional acid or base is added to the solution.

Biochemical reactions: Biological, chemical, or biochemical reactions involve the formation or cleavage of ionic and/or covalent bonds.

Reactive: A compound is reactive if it is capable of forming either an ionic or a covalent bond with another compound. The portions of reactive compounds that are capable of forming covalent bonds are referred to as reactive functional groups.

Steroid: A steroid derivative means a sterol, a sterol in which the hydroxyl moiety has been modified (for example, acylated), or a steroid hormone, or an analog thereof. The modification can include spacer groups, linkers, or reactive groups.

Sterics: Steric hindrance, or sterics, is the prevention or retardation of a chemical reaction because of neighboring groups on the same molecule.

EXAMPLES

Figure 2:
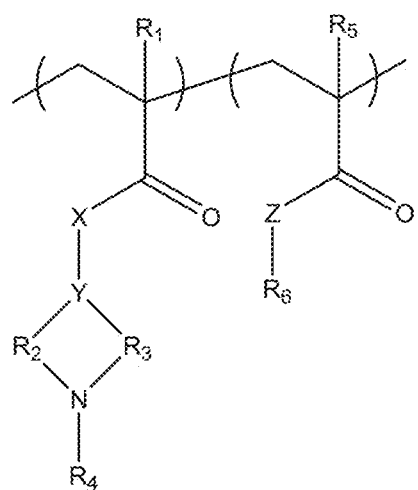
FIG. 2 shows the general structure of cationic cyclic amine containing acrylamide/acrylate and alkyl acrylamide/acrylate copolymers.

Polymers with a (meth)acrylate or (meth)acrylamide backbone and a cyclic amine containing side group (three or more carbons) containing one or more secondary or tertiary amines are described (FIG. 1). The copolymers can be a combination of two or more different cationic repeat unit structures, or can be a combination of (meth)acrylamide and (meth)acrylate cationic units (FIG. 1). Copolymers can be a combination of (meth)acrylate or (meth)acrylamide cyclic amine containing cationic units and alkyl (meth)acrylate or (meth)acrylamide units (FIG. 2).

Figure 3:
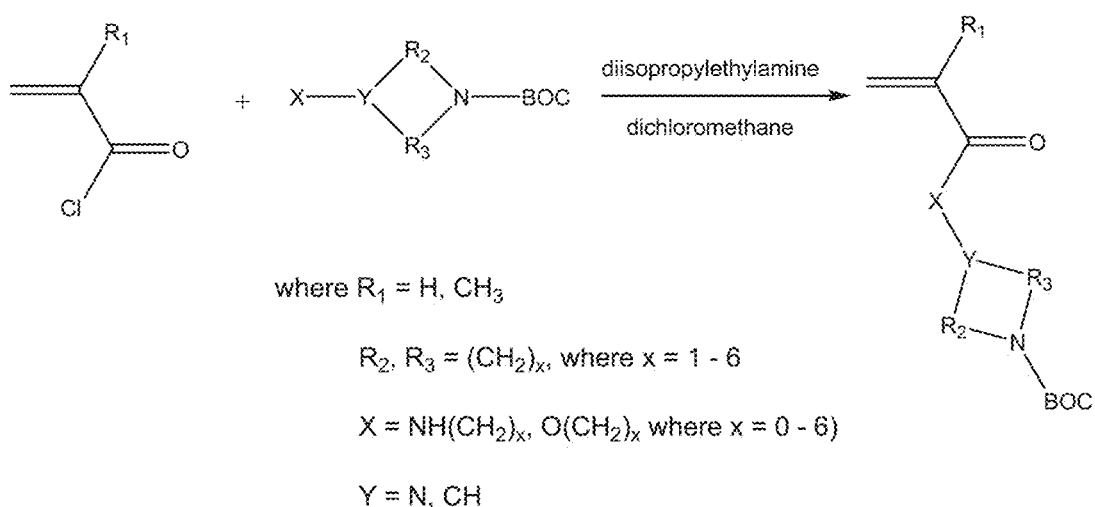
FIG. 3 shows the general method for synthesizing tert-Butyloxycarbonyl (BOC) protected cyclic amine containing monomers.
Figure 4:
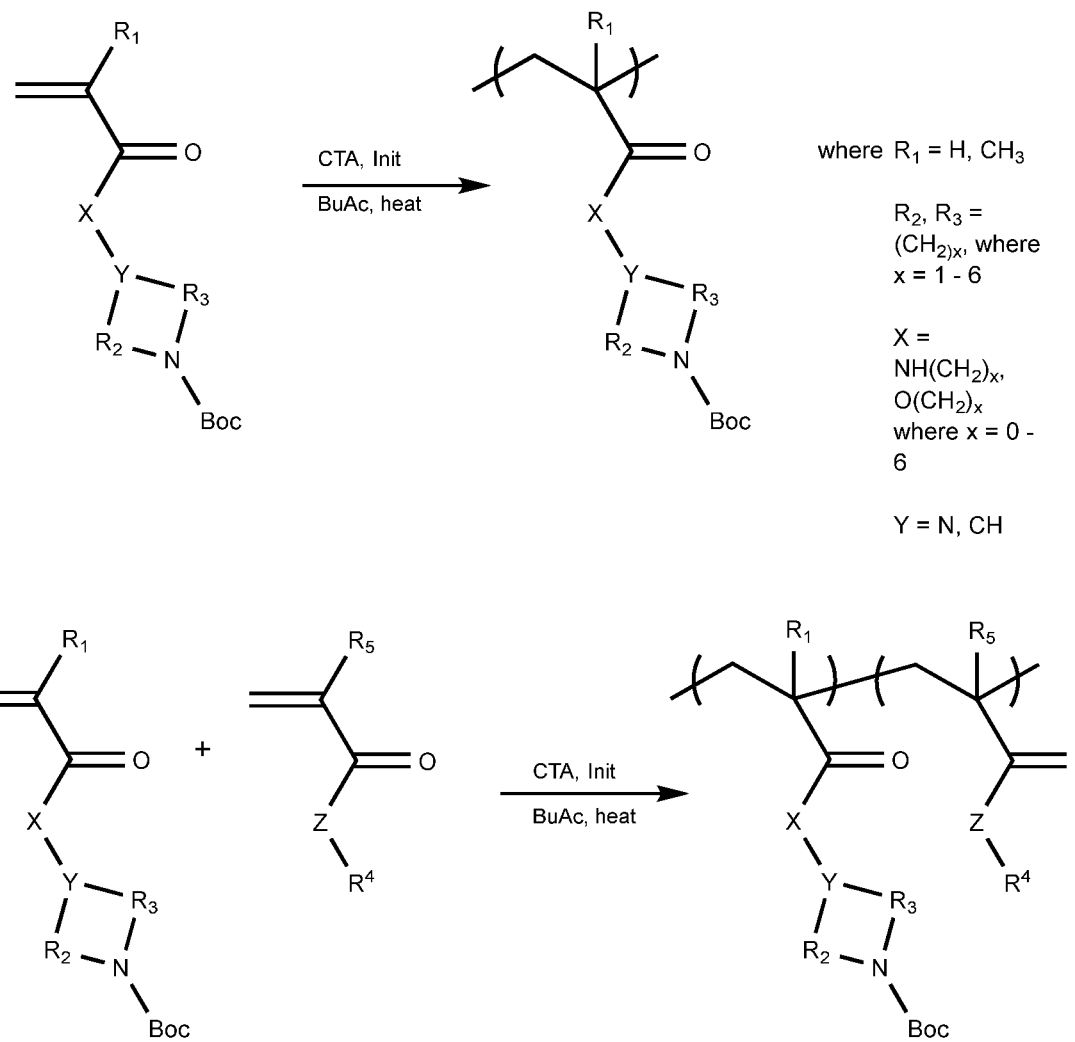
FIG. 4 shows RAFT polymerization of BOC protected monomers in the presence of a chain transfer agent (CTA), free radical initiator (Init), solvent (e.g. butyl acetate, BuAc), and heat (60-100 C).
Figure 5:
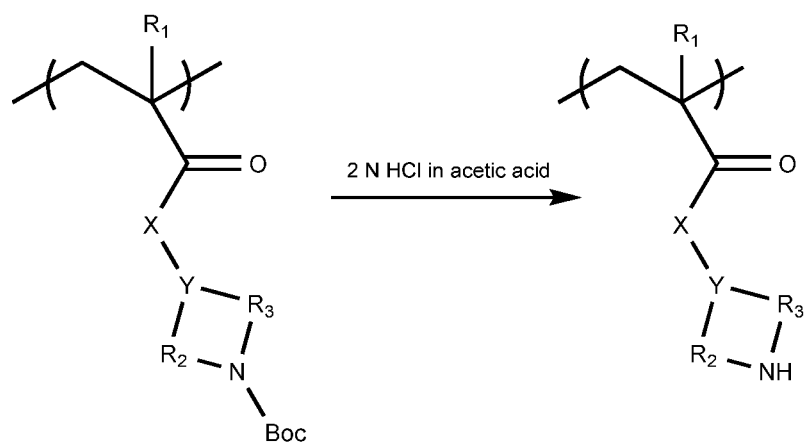
FIG. 5 shows the removal of BOC protecting groups to form cationic polymers with cyclic amine moieties.
Figure 6:
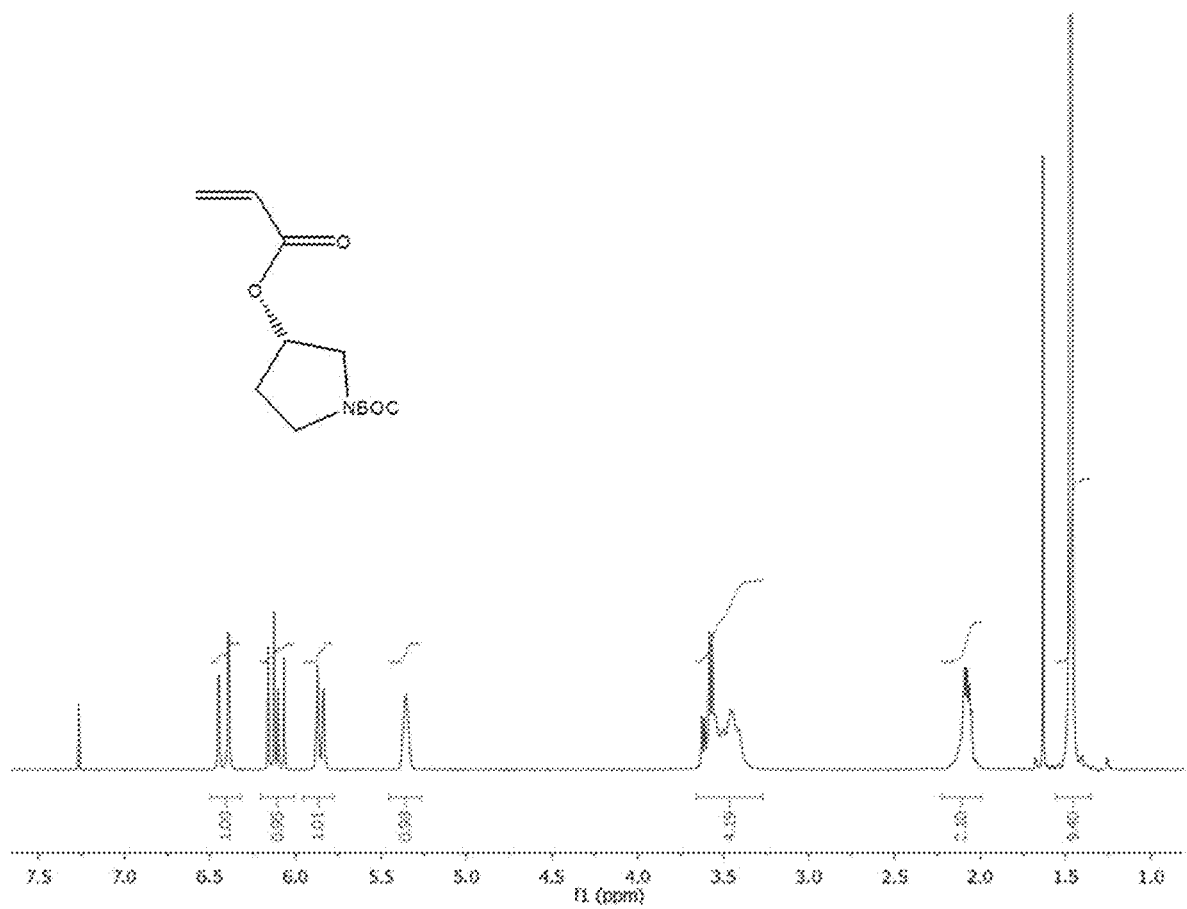
FIG. 6 shows the $^1$H NMR of (S)—N—BOC-pyrrolidinyl acrylate in CDCl$_3$.
Figure 7:
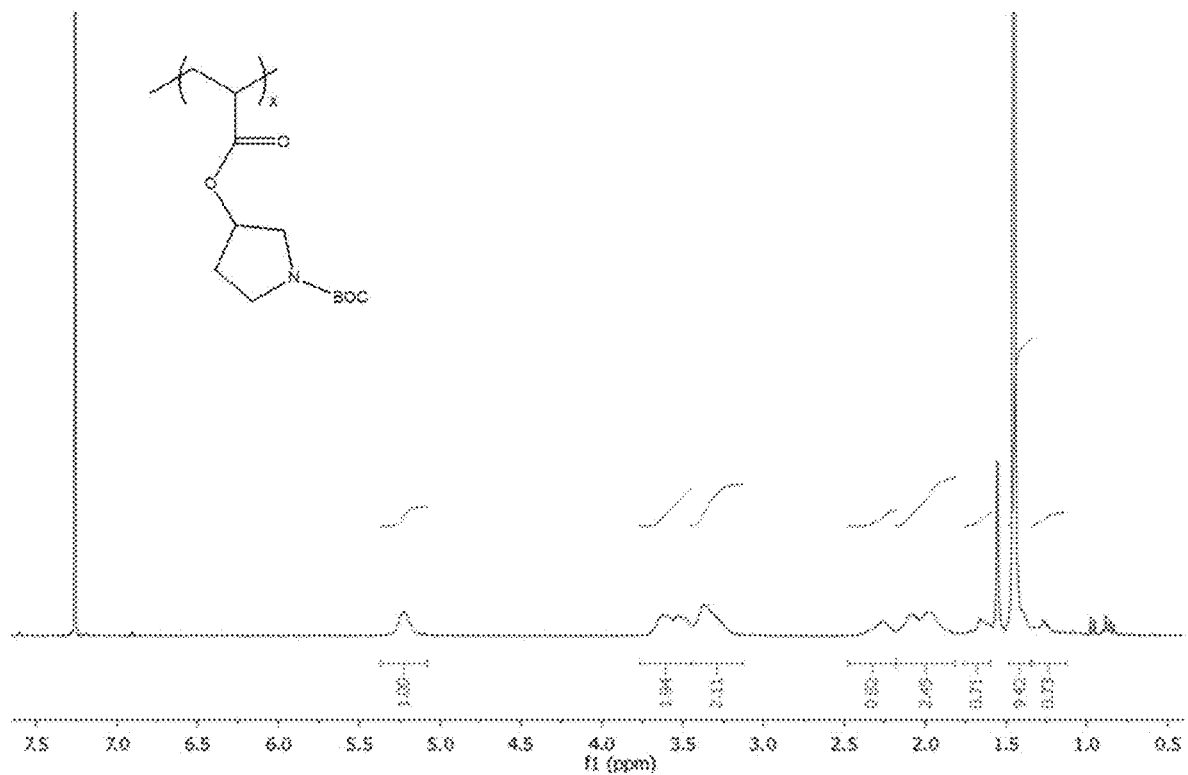
FIG. 7 shows the $^1$H NMR of poly((S)—N—BOC-pyrrolidinyl acrylate) in CDCl$_3$.
Figure 8:
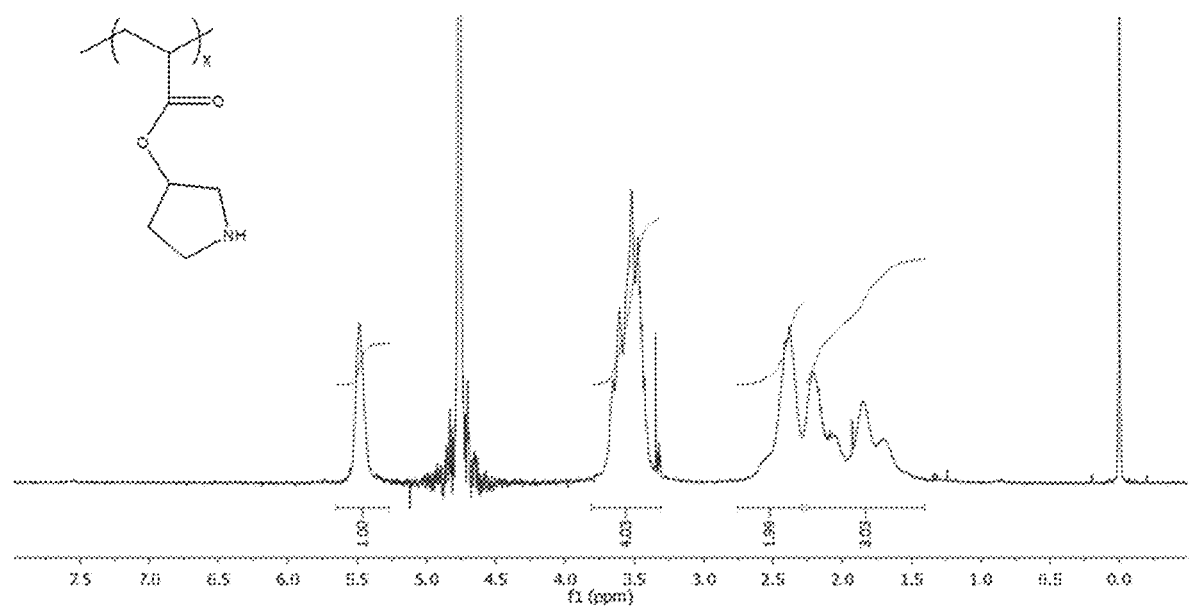
FIG. 8 shows the $^1$H NMR of poly((S)-pyrrolidinyl acrylate) in D$_2$O.

FIG. 3 highlights the tert-Butyloxycarbonyl (BOC) protected cyclic amino acrylate and acrylamide monomers synthesized and polymerized by Minis Bio LLC. The monomers are synthesized by reacting acryloyl chloride or methacryloyl chloride with either hydroxyl groups or amines (primary or secondary) in the presence of a base (usually diisopropylethylamine) and solvent (usually dichloromethane). Structure and purity of the monomers is determined by $^1$H NMR (FIG. 6). These monomers then undergo polymerization and copolymerization (FIG. 4). In this instance, the RAFT polymerization process is shown. Once the (co) polymers are purified by precipitation (usually into hexane), they are analyzed by gel permeation chromatography (organic solvent phase) and $^1$H NMR (FIG. 7). The (co) polymers are deprotected under acidic conditions to remove the BOC protecting groups (FIG. 5); structure and purity confirmed by $^1$H NMR (FIG. 8).

All BOC protected cyclic amine containing monomers were synthesized based on the reaction of either acryloyl chloride or methacryloyl chloride with a primary amine containing moiety in the presence of a base (FIG. 3). The synthesis of 1-(N—BOC-piperidyl)-4-acrylamide (14PipAm) is described here as an example:

4-amino-1-boc-piperidine (5.00 g, 0.025 mol) was dissolved in dichloromethane (50 mL) and added to a dry 250 mL 3 neck round bottom flask flushed with nitrogen and equipped with a dropping funnel and stirrer bar. The flask was immersed in an ice bath before acryloyl chloride (2.47 g, 0.0272 mol) in dichloromethane (15 mL) was added to the stirring solution drop-wise via the dropping funnel over a period of 45 min. The solution was stirred overnight and allowed to warm to room temperature. The solution was washed with 10% w/v citric acid solution (20 mL), 10% potassium carbonate solution (20 mL), saturated sodium bicarbonate solution (20 mL), and brine (20 mL). The organic layer was then dried over sodium sulfate and passed through a basic alumina plug. The solvent was then removed by rotor evaporation at room temperature. The oil product was dissolved in dichloromethane (10 mL) and precipitate three times into hexane. If necessary, a silica column is also used to purify the monomer. Yield=4.0 g (63%). $^1$H NMR, $\delta$(CDCl$_3$) ppm: 1.32 (2H), 1.45 (9H), 1.95 (2H), 2.87 (2H), 4.03 (3H), 5.52 (1H), 5.66 (1H), 6.10 (1H), 6.30 (1H).

Example 1

Polymer synthesis: The monomers described were polymerized using RAFT in order to synthesize polymers of well-defined molecular weights, compositions, and architectures. The synthesis of poly(1-piperidyl)-4-acrylamide) (P14PipAm) is given as an example.

1-(N—BOC-piperidyl)-4-acrylamide (0.200 g, 0.787 mmol), 4-cyano-4(phenylcarbonothioylthio)pentanoic acid (CPCPA, 1.12 mg, 0.00401 mmol), AIBN (0.098 mg, 0.00060 mmol), and butyl acetate (1.00 mL) were added to a 20 mL glass vial with stirrer bar. The vial was sealed with a rubber cap and the solution bubbled with nitrogen using a long syringe with a second syringe as the outlet for 1 h. The syringes were removed and the vial heated to 80° C. for 15 h using an oil bath. The solution was allowed to cool to room temperature and precipitated into hexane. The product was re-dissolved in dichloromethane and precipitated into hexane dried under reduced pressure for several hours. Yield=0.181 mg (90%). $^1$H NMR, $\delta$(CDCl$_3$) ppm: 1.4 (9H), 1.8 (3H), 2.2 (2H), 2.8 (2H), 3.8 (2H), 4.0 (3H).

The BOC protected polymers were deprotected post-polymerization to yield primary and secondary amines in the polymer side groups. The deprotection of P14PipAm-BOC is described as an example.

P14PipAm-BOC (0.150 g) was dissolved in a 2N HCl solution of acetic acidic (4 mL) and stirred for 1 h. Water (15 mL) was added to the solution, which was then dialyzed against salt water and then deionized water over a period of 48 h. The dialyzed solution was then frozen and lyophilized to dryness (Yield=0.080 g).

Example 2

Lipid synthesis: To a cooled solution of 1,4-bis(aminoalkyl)piperazine (1 eq) and Et3N (2.1 eq) in CHCl3 is added, dropwise, a solution of acyl chloride (2.05-2.1 eq) in CHCl3. The reaction mixture is stirred at room temperature overnight. The reaction mixture is diluted with CHCl3 to double the volume, washed three times with saturated Na2CO3, washed once with saturated NaCl, and dried with MgSO4 or Na2SO4. The solvent is removed using a rotary evaporator. The bisamide is purified by recrystallization or by column chromatography.

Figure 9:
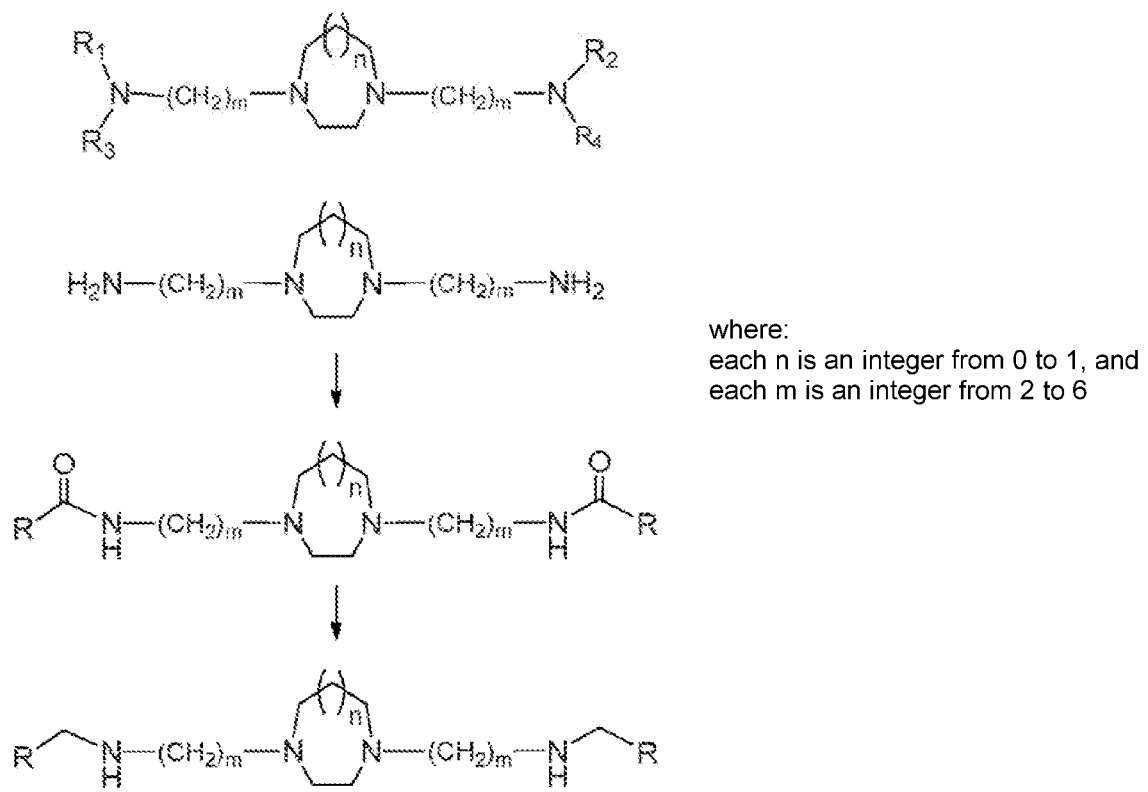
FIG. 9 shows the general experimental for piperazine [and homopiperazine] based compounds (n=1, 2; R$_1$ & R$_2$=hydrocarbon; R$_3$ & R$_4$=—C(=O)—R5).

To a stirred suspension of lithium aluminum hydride (LAH, 3 eq) in tetrahydrofuran (THF), under nitrogen, is added, dropwise, a solution of bisamide (1 eq) in THF. When the addition is complete, the reaction mixture is refluxed under nitrogen overnight. Then the reaction mixture is cooled (cold water bath), and excess hydride is decomposed following standard procedure(s). The mixture is filtered, and the precipitate is washed with THF. The filtrate is diluted with CHCl3 to at least double the volume, washed twice with water, washed once with saturated NaCl, and dried with MgSO4 or Na2SO4. The solvents are removed using a rotary evaporator. The amine is purified by column chromatography. (see FIG. 9)

(Bis-His-ODAP) To a solution of 155.1 mg (2.211×10-4 mol) of ODAP in 6 mL of THF was added 80.9 μL (4.645×10-4 mol) of DIEA, followed by 210.1 mg (4.644×10-4 mol) of Boc-His(1-Boc)-OSu. The reaction mixture was stirred at room temperature overnight (20 hr). Then the reaction mixture was diluted with 50 mL of CHCl3, washed with saturated Na2CO3 (3×25 mL), washed with water (25 mL), washed with saturated NaCl (25 mL), dried with MgSO4, and evaporated. Column chromatography on silica gel with CHCl3/MeOH=93:7 afforded 203.7 mg (67%) of Bis-(Boc-His(1-Boc))-ODAP as an oil: Rf=0.26 (CHCl3/MeOH=93:7), 0.49 (CHCl3/MeOH=90:10) (I2 or KMnO4); 1H NMR (400 MHz, CDCl3, TMS) δ 7.97 (s, 2H), 7.14 (s, 2H), 5.4-5.3 (m, 6H, alkene-H+NH), 4.9-4.8 (m, 2H), 3.6-3.3 (m, 4H), 3.3-3.0 (m, 4H), 3.0-2.7 (m, 4H), 2.6-2.2 (m, 8H), 2.3-2.2 (m, 4H), 2.1-2.0 (m, 8H), 1.8-1.6 (m, 4H), 1.59 (s, 18H), 1.5-1.4 (m, 4H), 1.39 (s, 18H), 1.4-1.2 (m, 44H), 0.88 (t, J=6.8 Hz, 6H); MS (ESI) m/z 1376.1 (M+), 1276.0 ([M-Boc]+), 688.6 (M+2), 638.6 ([M-Boc]+2).

To a solution of 196.5 mg (1.428×10-4 mol) of Bis-(Boc-His(1-Boc))-ODAP in 12 mL of THF was added 6 mL of 6N HCl. After stirring at room temperature overnight, the reaction mixture was rotovapped. The crude HCl salt was purified by column chromatography on silica gel with CHCl3/MeOH/NH4OH=85:15:2 to afford 115.0 mg (83%) of Bis-His-ODAP as a colorless oil: Rf=0.09 (CHCl3/MeOH/NH4OH=85:15:2), (ninhydrin, I2 or KMnO4); 1H NMR (400 MHz, CDCl3, TMS) δ5.4-5.3 (m, 4H), 4.1-4.0 (m, 2H, αH), 3.5-3.1 (m, 8H), 3.0-2.7 (m, 4H) 2.5-2.1 (m, 12H), 2.1-2.0 (m, 8H), 1.8-1.6 (m, 4H), 1.6-1.4 (m, 4H), 1.4-1.2 (m, 44H), 0.88 (t, J=7.0 Hz, 6H); MS (MALDI) m/z 975.77 (M+).

(Bis-(N-MeHis)-ODAP) To a solution of 437.8 mg (8.556×10-4 mol) of Boc-N-Me-His(Trt)-OH and 260.9 mg (3.730×10-4 mol) of ODAP was added 327.9 μL (1.883 mmol) of DIEA, and then 261.5 mg (1.027 mmol) of BOP—Cl. After stirring at room temperature for 1.5 hr, the reaction mixture was partitioned between 50 mL of CHCl3 and 25 mL of water. The CHCl3 phase was dried with MgSO4, and evaporated. Column chromatograpy on silica gel with 5% MeOH in CHCl3 afforded 586.4 mg (93%) of Bis-(Boc-N-Me-His(Trt))-ODAP as an oil: Rf=0.25 (CHCl3/MeOH=95:5) (UV, I2); 1H NMR (400 MHz, CDCl3, TMS) δ 7.4-7.3 (m, 20H), 7.2-7.1 (m, 12H), 6.57 (br s, 2H), 5.4-5.3 (m, 5H), 5.2-5.1 (m, 1H), 3.6-3.3 (m, 4H), 3.3-3.1 (m, 4H), 3.1-2.8 (m, 4H), 2.77 (s, 3H), 2.74 (s, 3H), 2.6-2.2 (m, 8H), 2.3-2.2 (m, 4H), 2.1-2.0 (m, 8H), 1.8-1.6 (m, 4H), 1.5-1.4 (m, 4H), 1.37 (s, 18H), 1.4-1.2 (m, 44H), 0.88 (t, J=7.0 Hz, 6H).

Figure 10:
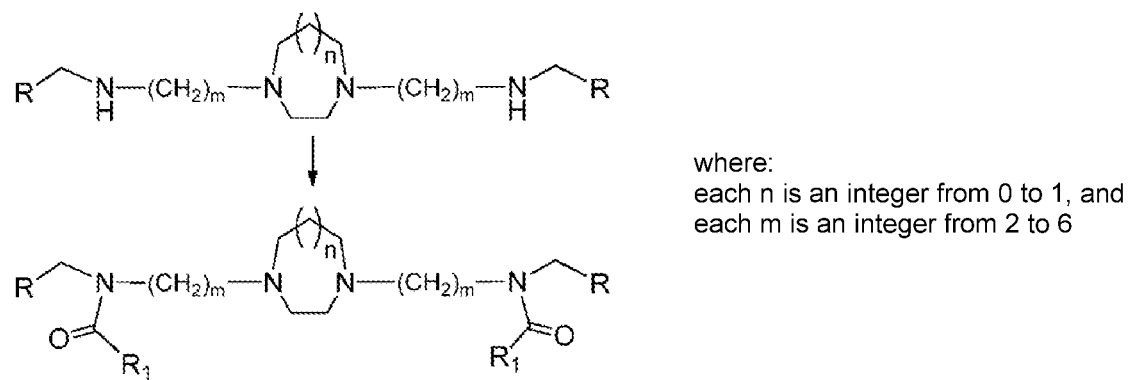
FIG. 10 shows amide bond formation.

To a 100 mL rb flask containing 580.5 mg (3.438×10-4 mol) of Bis-(Boc-N-Me-His(Trt))-ODAP was added 13 mL of 95% TFA. The material was dissolved, and stirred at room temperature. After 45 min, the solvent was evaporated, and the residue was dried under vacuum. Column chromatography on silica gel with CHCl3/MeOH/NH4OH=90:10:1 then 85:15:1 afforded 243.1 mg (70%) of Bis-(N-MeHis)-ODAP as an oil: Rf=0.13 (CHCl3/MeOH/NH4OH=90:10:1), 0.33 (CHCl3/MeOH/NH4OH=85:15:1) (I2); 1H NMR (400 MHz, CDCl3, TMS) δ 7.6-7.5 (m, 2H). 6.9-6.8 (m, 2H), 5.4-5.3 (m, 4H), 5.1-5.0 (m, 2H), 3.7-3.5 (m, 4H), 3.5-3.2 (m, 4H), 3.0-2.7 (m, 4H), 2.6-2.2 (m, 12H), 2.36 (s, 3H), 2.34 (m, 3H), 2.1-2.0 (m, 8H), 1.8-1.6 (m, 4H), 1.6-1.4 (m, 4H), 1.4-1.2 (m, 44H), 0.88 (t, J=6.8 Hz, 6H); MS (MALDI) m/z 1003.9547 (M+), 1021.9617 ([M+H2O]+). (see FIG. 10)

Example 3

Transfection efficiency of cationic cyclic amine polymers and Bis-δ-Ava-ODAP or bis-(linoleyl)-4P4 relative to a commercially available reagent.

All transfections were performed in triplicate in 96 well plates using suspension 293-F cells grown in serum-free complete media. Cells were seeded at 500,000 cells/mL at time of transfection. Transfection competent complexes were prepared by first mixing 0.1 ug (per well) plasmid DNA (pCIluc-luciferase expression plasmid) with 10 μl Opti-MEM reduced serum media, followed by sequential addition of the polycation (cationic cyclic amines 3103 and 3301) and amphipathic compound (1112 or 1180). Ternary complexes were incubated for 20 minutes before drop-wise addition to cultured cells. Cultured cells were grown in 100 μL serum-free complete media. No media change is required post-transfection.

Figure 11:
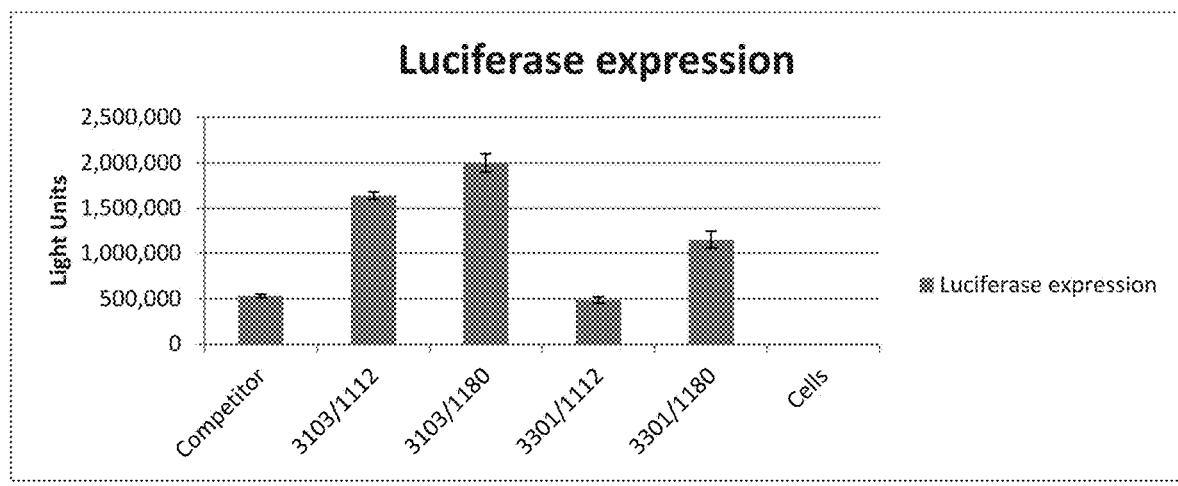
FIG. 11 shows data from an experiment comparing the claimed cyclic amines and standard lipids with a competitor's transfection reagent and the same lipids.
Figure 11:
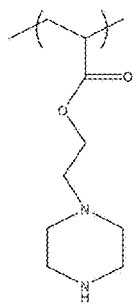
Figure 11:
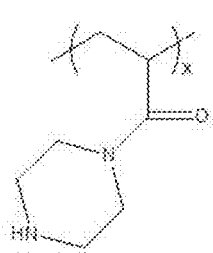
Figure 11:
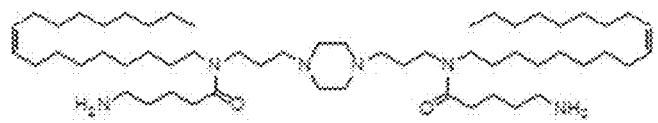
Figure 11:
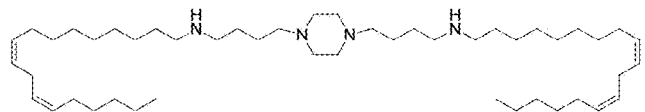

In this example cationic cyclic amines 3103 or 3301 served as the polycation and Bis-δ-Ava-ODAP (1112) or Bis-(linoleyl)-4P4 (1180) served as the amphipathic compound. Comparisons were made with the commercially available reagent jetPEI® (Polyplus Transfection) according to the manufacturer's recommended protocol (FIG. 11). Cells were harvested at 36 hours and assayed for luciferase activity. FIG. 11 depicts the mean relative light units for each experimental condition. The error bars represent the standard deviation of the triplicate wells.

At optimal dose and ratio, the combination of cationic cyclic amine 3103 and amphipathic 1180 resulted up to a 4-fold increase in relative light units versus commercially available reagents. This demonstrates the transfection efficiency of cationic cyclic amine 3103+Bis-(linoleyl)-4P4 when complexed with pDNA and transfected into cells in culture.

TABLE 1

| Structure of cationic polymer side chains | | | | | | | |
|---|---|---|---|---|---|---|---|
| Polymer | Nomenclature | $R_1$ | $R_2$ | $R_3$ | X | Y | Monomer Structure |
| 1 | R2PA | H | $(CH_2)_2$ | $CH_2$ | O | CH | |

TABLE 1-continued

Structure of cationic polymer side chains

| Polymer | Nomenclature | R₁ | R₂ | R₃ | X | Y | Monomer Structure |
|---|---|---|---|---|---|---|---|
| 2 | S2PA | H | (CH₂)₂ | CH₂ | O | CH | |
| 3 | 14PipA | H | (CH₂)₂ | (CH₂)₂ | O | CH | |
| 4 | 14PipMA | CH₃ | (CH₂)₂ | (CH₂)₂ | O | CH | |
| 5 | R1PipA | H | (CH₂)₃ | CH₂ | O | CH | |
| 6 | S1PipA | H | (CH₂)₃ | CH₂ | O | CH | |
| 7 | PipzA | H | (CH₂)₂ | (CH₂)₂ | — | N | |

TABLE 1-continued

Structure of cationic polymer side chains

| Polymer | Nomenclature | $R_1$ | $R_2$ | $R_3$ | X | Y | Monomer Structure |
|---|---|---|---|---|---|---|---|
| 8 | PipEtA | H | $(CH_2)_2$ | $(CH_2)_2$ | O | $(CH_2)_2N$ | |
| 9 | PipPrA | H | $(CH_2)_2$ | $(CH_2)_2$ | O | $(CH_2)_3N$ | |
| 10 | PipAm | H | $(CH_2)_2$ | $(CH_2)_2$ | NH | CH | |
| 11 | PipMeAm | H | $(CH_2)_2$ | $(CH_2)_2$ | NH | $(CH_2)_2$ | |
| 12 | PipMAm | $CH_3$ | $(CH_2)_2$ | $(CH_2)_2$ | NH | CH | |

TABLE 1-continued

Structure of cationic polymer side chains

| Polymer | Nomenclature | $R_1$ | $R_2$ | $R_3$ | X | Y | Monomer Structure |
|---|---|---|---|---|---|---|---|
| 13 | HHAzAm | H | $(CH_2)_3$ | $(CH_2)_2$ | NH | CH | 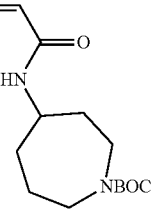 |

Example 4

Transfection efficiency of EPEI and Bis-(N-MeHis)-ODAP (1161) relative to commercially available reagents.

All transfections were performed in triplicate in 96 well plates using (A) primary Human Umbilical Vein Endothelial Cells (HUVEC) or (B) JAWS II cells. Cells were approximately 70% confluent at time of transfection. Transfection competent complexes were prepared by first mixing 0.1 ug (per well) plasmid DNA (pCIluc-luciferase expression plasmid) with 10 μl Opti-MEM reduced serum media, followed by sequential addition of the polycation and amphipathic compound. Ternary complexes were incubated for 20 minutes before drop-wise addition to cultured cells. Cultured cells were grown in 100 μL of appropriate media supplemented with 10% FBS. No media change is required post-transfection.

Figure 12:
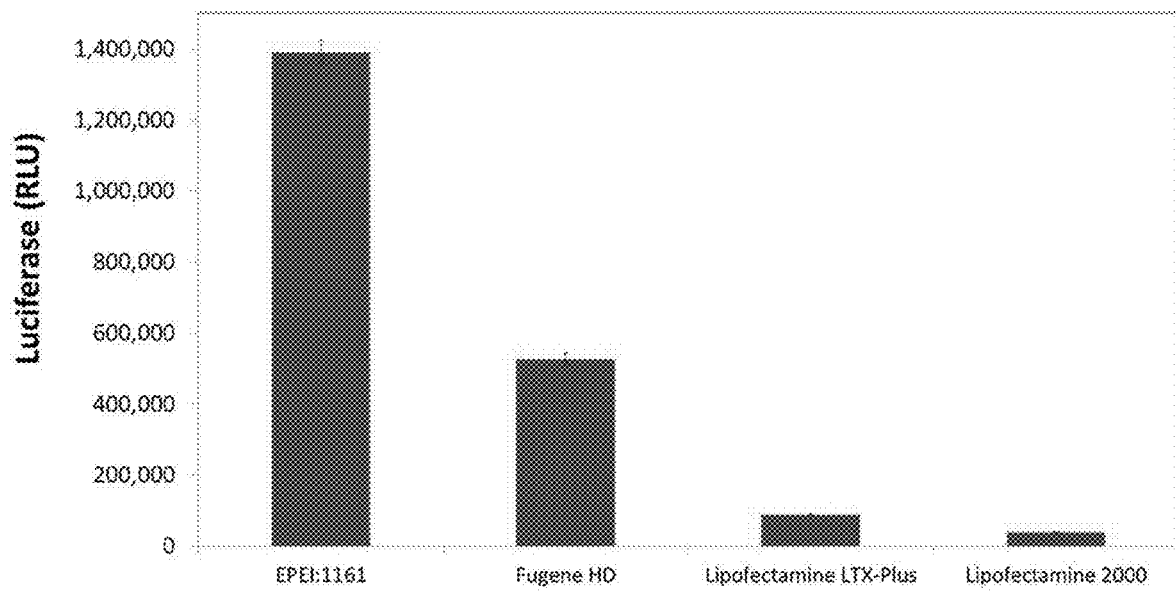
FIG. 12 shows data from an experiment comparing the claimed lipid with multiple competitor reagents using cell line A and cell line B.
Figure 12:
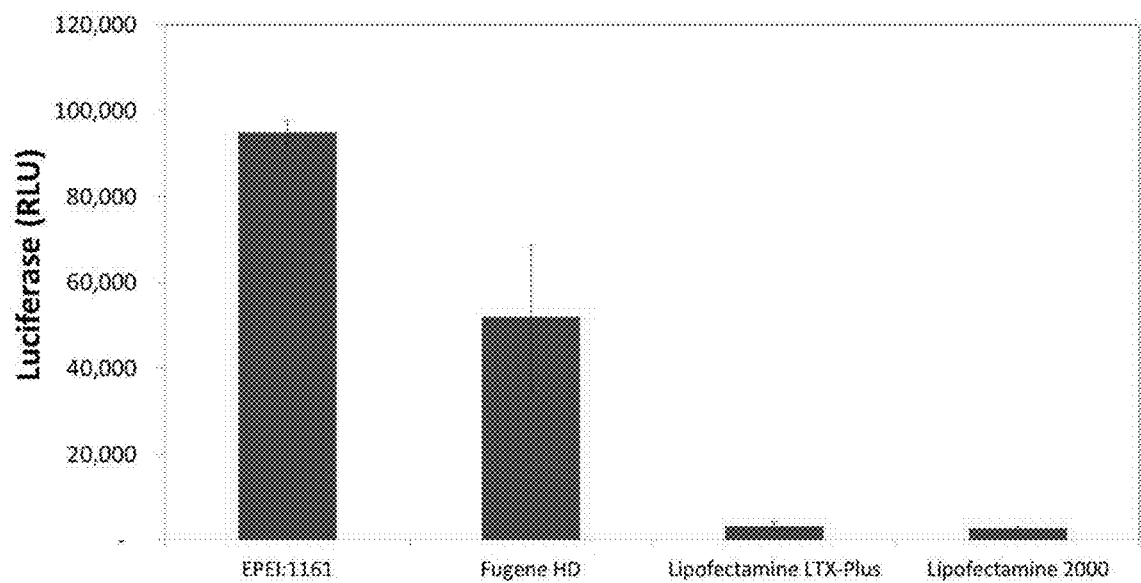
Figure 13:
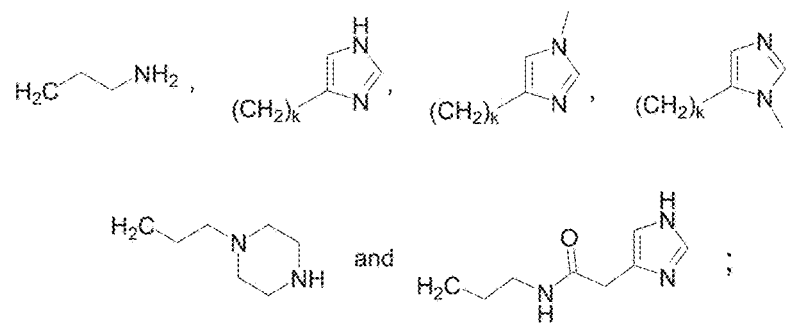
FIG. 13 shows representative R$_3$ and R$_4$ groups of the lipid transfection reagent.
Figure 14:
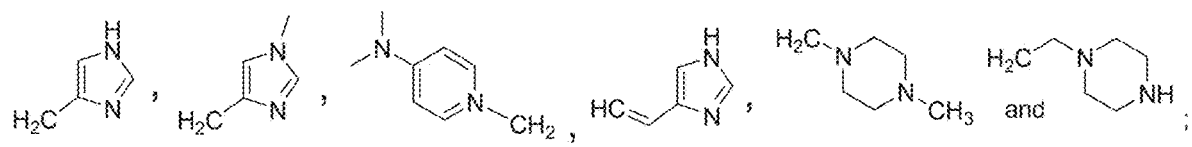
FIG. 14 shows representative R$_6$ groups of the lipid transfection reagent.

In this example EPEI served as the polycation and Bis-(N-MeHis)-ODAP (in FIG. 12 noted as 1161) served as the amphipathic compound. Comparisons were made with several commercially available reagents using optimized ratios of reagent to DNA and following the manufacturer's recommended protocol (FIG. 12). Commercially available reagents included Fugene® HD (Promega), Lipofectamine® 2000 (Life Technologies) and Lipofectamine® LTX Plus (Life Technologies). Cells were harvested at 24 hours and assayed for luciferase activity. FIG. 12 depicts the mean relative light units for each experimental condition. The error bars represent the standard deviation of the triplicate wells.

At optimal dose and ratio, EPEI+Bis-(N-MeHis)-ODAP resulted in up to 36-fold increase in relative light units versus commercially available reagents. This demonstrates the transfection efficiency of EPEI+Bis-(N-MeHis)-ODAP when complexed with pDNA and transfected into cells in culture.

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A composition for delivery of a nucleic acid into a cell comprising:
   (i) a polymer comprising a first cyclic amine; and
   (ii) an amphipathic compound comprising a second cyclic amine;
   wherein said polymer is different from said amphipathic compound.

2. The composition of claim 1, wherein said first cyclic amine comprises (1) two or more carbons and (2) at least one secondary or tertiary amine.

3. The composition of claim 1, wherein said first cyclic amine comprises a structure of:

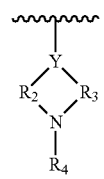

wherein:
   $R_2$ and $R_3$ are each $(CH_2)_x$, wherein each x is independently 1, 2, 3, 4, 5, or 6;
   Y is N or CH; and
   $R_4$ is H or $CH_3$.

4. The composition of claim 3, wherein each x is independently 1, 2, or 3; and $R^4$ is H.

5. The composition of claim 1, wherein said polymer comprises a polyacrylate or a polyacrylamide.

6. The composition of claim 1, wherein said polymer comprises 2 to about 80 monomeric units.

7. The composition of claim 1, wherein said polymer comprises greater than 80 monomeric units.

8. The composition of claim 1, wherein said polymer comprises a copolymer.

9. The composition of claim 8, wherein said first cyclic amine comprises a 5- to 7-membered cyclic amine.

10. The composition of claim 8, wherein said copolymer comprises a first monomeric unit comprising said first cyclic amine, and a second monomeric unit comprising at least one secondary or tertiary amine.

11. The composition of claim 10, wherein said second monomeric unit comprises a structure of:

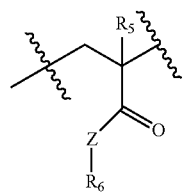

wherein:

$R_5$ is H or $CH_3$, $R_6$ is an alkyl group containing one or more primary, secondary, or tertiary amines, and Z is NH or O.

12. The composition of claim 8, wherein said copolymer is a block copolymer, an alternating copolymer, a random or statistical copolymer, or a gradient copolymer.

13. The composition of claim 8, wherein said copolymer has a linear structure, a graft structure, a branched structure, a crosslinked or network structure, a star structure, a comb structure, a ladder structure, or a dendritic structure.

14. The composition of claim 1, wherein said second cyclic amine comprises a structure of:

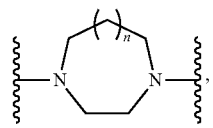

wherein n is 0 or 1.

15. The composition of claim 1, further comprising said nucleic acid molecule.

16. The composition of claim 15, wherein said nucleic acid molecule comprises DNA, RNA, or any combination thereof.

17. The composition of claim 16, wherein said RNA comprises mRNA.

18. A method of delivering a nucleic acid molecule into a cell, comprising:
   (a) providing a composition comprising:
      (i) a polymer comprising a cyclic amine;
      (ii) an amphipathic compound; and
      (iii) said nucleic acid molecule; and
   (b) bringing said composition in contact with said cell, thereby delivering said nucleic acid molecule into said cell.

19. The method of claim 18, wherein said nucleic acid molecule comprises DNA or RNA.

20. The method of claim 18, wherein said nucleic acid molecule is delivered into said cell in vitro or in vivo.

* * * * *